(12) United States Patent
Borch et al.

(10) Patent No.: US 7,951,267 B2
(45) Date of Patent: May 31, 2011

(54) ENZYMATIC HYDROLYSIS OF A POLYMER COMPRISING VINYL ACETATE MONOMER

(76) Inventors: Kim Borch, Davis, CA (US); Henrik Lund, Skodsborg (DK); Masaki Sharyo, Matsudo (JP); Hiromichi Sakaguchi, Chiba (JP); Hanne Host Pedersen, Lyngby (DK); James William Fitzhenry, Memphis, TN (US)

( * ) Notice: Subject to any disclaimer, the term of this patent is extended or adjusted under 35 U.S.C. 154(b) by 452 days.

(21) Appl. No.: 11/626,027

(22) Filed: Jan. 23, 2007

(65) Prior Publication Data

US 2008/0023160 A1 Jan. 31, 2008

Related U.S. Application Data

(63) Continuation of application No. 10/846,123, filed on May 14, 2004, now abandoned, which is a continuation of application No. 10/152,300, filed on May 21, 2002, now abandoned.

(60) Provisional application No. 60/294,539, filed on May 30, 2001.

(30) Foreign Application Priority Data

May 21, 2001 (DK) .................................. 2001 00813

(51) Int. Cl.
- *D21H 21/02* (2006.01)
- *D21H 17/00* (2006.01)
- *D21C 5/02* (2006.01)
- *C12N 9/00* (2006.01)

(52) U.S. Cl. ................ 162/199; 162/5; 162/72; 510/174
(58) Field of Classification Search ................ 162/9, 72, 162/141, 149, 158, 183, 189, 4–5, 70, 199; 435/128, 210, 70.3, 262–263, 198, 277–278; 510/174

See application file for complete search history.

(56) References Cited

U.S. PATENT DOCUMENTS

| | | | |
|---|---|---|---|
| 5,116,474 A | 5/1992 | Fuentes et al. | |
| 5,176,796 A | 1/1993 | Irie et al. | |
| 5,256,252 A | 10/1993 | Sarkar et al. | |
| 5,667,634 A | 9/1997 | Fujita et al. | |
| 5,766,926 A * | 6/1998 | Blanchette et al. | 435/253.3 |
| 5,856,163 A | 1/1999 | Hashida et al. | |
| 5,892,013 A | 4/1999 | Svendsen | |
| 6,099,688 A | 8/2000 | Pere et al. | |
| 6,441,849 B1 | 8/2002 | Fukuda | |
| 6,468,391 B1 | 10/2002 | Sharyo et al. | |
| 6,471,826 B2 | 10/2002 | Glover et al. | |
| 6,495,357 B1 | 12/2002 | Fuglsang et al. | |
| 7,067,244 B2 | 6/2006 | Jiang et al. | |
| 7,125,471 B2 * | 10/2006 | Hill et al. | 162/189 |
| 7,172,997 B2 * | 2/2007 | Minning et al. | 510/226 |
| 7,465,570 B2 * | 12/2008 | Borch et al. | 435/196 |
| 2002/0059998 A1 | 5/2002 | Glover et al. | |
| 2002/0084046 A1 | 7/2002 | Hsu et al. | |
| 2002/0162635 A1 | 11/2002 | Hsu et al. | |
| 2003/0046984 A1 | 3/2003 | Jiang et al. | |
| 2003/0051836 A1 | 3/2003 | Borch et al. | |
| 2003/0054539 A1 | 3/2003 | Schulein et al. | |
| 2003/0092097 A1 | 5/2003 | Andersen et al. | |
| 2003/0102095 A1 | 6/2003 | Hill et al. | |
| 2003/0124710 A1 | 7/2003 | Borch et al. | |
| 2003/0199069 A1 | 10/2003 | Fuglsang et al. | |
| 2004/0226672 A1 * | 11/2004 | Borch et al. | 162/72 |
| 2005/0000666 A1 * | 1/2005 | Taylor et al. | 162/24 |
| 2005/0003516 A1 * | 1/2005 | Lund et al. | 435/278 |
| 2007/0119559 A1 * | 5/2007 | Lund et al. | 162/147 |
| 2008/0023160 A1 * | 1/2008 | Borch et al. | 162/5 |
| 2008/0169073 A1 * | 7/2008 | Xu et al. | 162/199 |
| 2008/0283207 A1 * | 11/2008 | Thomas | 162/177 |
| 2008/0311242 A9 * | 12/2008 | Borch et al. | 426/20 |
| 2009/0047384 A1 * | 2/2009 | Bojsen et al. | 426/18 |
| 2009/0065159 A1 * | 3/2009 | Xu et al. | 162/78 |
| 2009/0203568 A1 * | 8/2009 | Souter et al. | 510/321 |
| 2009/0217463 A1 * | 9/2009 | Souter et al. | 8/137 |
| 2009/0217464 A1 * | 9/2009 | Souter et al. | 8/137 |
| 2009/0220480 A1 * | 9/2009 | Gray et al. | 424/94.61 |

FOREIGN PATENT DOCUMENTS

| | | |
|---|---|---|
| CA | 2412757 | 12/2001 |
| EP | 943678 A2 | 9/1999 |
| JP | 08014078 | 1/1990 |
| JP | 02160984 | 6/1990 |
| JP | 2229290 | 9/1990 |
| JP | 03124891 | 5/1991 |
| JP | 09241985 | 9/1997 |
| WO | WO 88/09367 A1 | 12/1988 |
| WO | WO 89/09263 A1 | 10/1989 |
| WO | WO 92/13130 A1 | 8/1992 |
| WO | WO 94/14964 A1 | 7/1994 |
| WO | WO 94/25578 A1 | 11/1994 |
| WO | WO 98/36086 A1 | 8/1998 |
| WO | WO 00/34450 A1 | 6/2000 |
| WO | WO 01/92502 A1 | 12/2001 |
| WO | WO 01/98579 A2 | 12/2001 |
| WO | WO 02095127 A2 * | 11/2002 |
| WO | WO 2004092479 A2 * | 10/2004 |
| WO | WO 2007095575 A1 * | 8/2007 |

OTHER PUBLICATIONS

Leblanc et al., "Short chain fatty acid esters synthesis by commercial lipases in low-water systems and by resting microbial cells in aqueous medium", Biotechnology Letters, vol. 20, No. 12, pp. 1127-1131 (1998).

Masse et al., "Testing of alkaline and enzymatic hydrolysis pretreatments for fat particles in slaughterhouse wastewater", Bioresource Technology, vol. 77, pp. 145-155 (2001).

* cited by examiner

*Primary Examiner* — José A Fortuna
(74) *Attorney, Agent, or Firm* — Michael W. Krenicky (57) ABSTRACT

The invention relates to the use of certain lipolytic enzymes such as cutinases and lipases in the manufacture of paper and paper products from recycled paper. Examples of such enzymes are derived from strains of *Humicola*, *Candida*, *Fusarium* and *Pseudomonas*. By use of these enzymes, the problems relating to the so-called "stickies" derived from waste paper are reduced.

15 Claims, 1 Drawing Sheet

ENZYMATIC HYDROLYSIS OF A POLYMER COMPRISING VINYL ACETATE MONOMER

CROSS-REFERENCE TO RELATED APPLICATIONS

This application is a Continuation of U.S. patent application Ser. No. 10/846,123 (now abandoned) filed on May 14, 2004, which is a continuation of U.S. patent application Ser. No. 10/152,300 (now abandoned) filed May 21, 2002, which claims priority or the benefit under 35 U.S.C. 119 of Danish application no. PA 2001 00813 filed May 21, 2001 and U.S. provisional application No. 60/294,539 filed May 30, 2001, the contents of which are fully incorporated herein by reference.

SEQUENCE LISTING

Applicants also enclose a Sequence Listing for the above-captioned application

TECHNICAL FIELD

This invention relates to the use of certain lipolytic enzymes in the manufacture of paper and paper products from recycled paper. By use of these enzymes, the problems relating to the so-called stickies derived from waste paper are reduced.

BACKGROUND ART

Polymers comprising vinyl acetate are very commonly used as an adhesive and coating material throughout industrial sectors (paper, textiles etc.). However, because of their adhesive properties these polymers often cause problems at later process stages.

For example, in the paper industry polymers comprising vinyl acetate are used as a binder and coating material. During recycling these polymers tend to agglomerate together with fibres and other substances to form so-called "stickies", which reduce the quality of the paper product and results in a significant downtime of the machine.

WO 00/34450, WO 01/92502 and U.S. Pat. No. 5,176,796 report the use of certain lipases and cutinases in the manufacture of paper, viz. for pitch control. According to the above U.S. patent, pitch is a natural constituent of wood, and triglyceride is a major component thereof.

WO 01/98579 discloses the use of lipase and/or esterase for control of the problem with stickies during recycling of paper. The lipases designated RESINASE A2X, and NOVOCOR ADL, are included for comparison purposes in Examples 1-3 herein.

BRIEF DESCRIPTION OF THE INVENTION

The invention relates to the use of a class of lipolytic enzymes in the manufacture of paper from recycled paper, as well as methods for making paper using this class of lipolytic enzymes. The class of lipolytic enzymes is defined by reference to certain tests for hydrolytic activity on polymers comprising vinyl acetate.

DETAILED DESCRIPTION OF THE INVENTION

Stickies

According to the Thesaurus of Pulp and Paper Terminology, 1991 (edited by Institute of Paper Science and Technology, Atlanta, US), the term stickies designates waste paper contaminants of an adhesive character causing sticking of paper-machine parts during reprocessing. As examples of such contaminants, ink, tar, and latex are mentioned.

Further examples of stickies are tacky agglomerates of fibres, adhesives, coatings, binders and other materials, which form in a recycled papermaking process. Accordingly, stickies are mainly of concern for paper manufacturing processes in which recycled paper is used.

Stickies are water insoluble and tend to agglomerate and deposit on various parts of the paper manufacturing equipment, thereby causing paper quality problems, breaks of the paper web, and costly downtime periods for cleaning the equipment. For example, stickies may deposit on the paper forming felts thereby rendering the drainage of water from the forming paper web less efficient, which again may give rise to problems as described above.

Stickies have been distinguished in various ways, e.g. by size, or by specific gravity:

Primary stickies are so small as to usually not cause any problems, whereas secondary stickies or macro stickies are larger and tend to deposit. Macro stickies are generally of such size as to be retained on fine screens. Example of fine screens are those having slots of about 50-200, 60-190, or 70-180, or 80-170, or 80-160, or of about 80-150 micrometer.

High density and low density stickies may under certain conditions be removable by various types of mechanical equipment, but problems remain in particular with the so-called neutral range density stickies, i.e. stickies of a specific gravity of about 0.9 to about 1.1, or about 0.95 to about 1.05, or about 0.98 to about 1.02.

The chemical composition of stickies from various parts of the world may vary, mainly depending on the characteristics of the local paper manufacturing processes. Likewise, for the same reason, the composition of stickies may vary from factory to factory.

The following components are examples of components, one or more of which are typically found in European stickies: Acrylic Resins, Poly Vinyl Acetate (PVAc), Styren Butadien Resin (SBR), Poly Ethylene (PE) and Poly Propylene (PP).

In the context of the present invention, focus is on polymers comprising vinyl acetate, stickies being one example of such polymers. A polymer comprising vinyl acetate monomer may be a poly (vinyl acetate) homopolymer (PVAc) comprising vinyl acetate monomers or it may be a copolymer comprising vinyl acetate and other monomers such as ethylene, methyl acrylate, vinyl laurate and t-decanoic acid, ethenyl ester. Blends and mixtures of various polymers, wherein at least one of the polymers comprises vinyl acetate monomers, are also included in the definition of "polymer comprising vinyl acetate" as used herein. The same holds true for mixtures thereof not only with other polymers, but with any other compound.

Various ways of controlling stickies have been developed, such as controlling the quality of the incoming recycled paper, various mechanical screening and centrifugal methods, and dispersion methods using various chemicals. Also the use of enzymes has been proposed (see e.g. WO 01/98579 referred to above).

However severe problems still remain, which—according to the invention—are diminished by the use of certain lipolytic enzymes, superior to the enzymes previously described for this purpose.

Lipolytic Enzymes

In the present context, the expression "lipolytic" enzyme refers to a class of enzymes having the unifying and characteristic feature that they are able to hydrolyse a polymer comprising vinyl acetate monomer.

For determining whether a given enzyme falls within this class of lipolytic enzymes, either of the following tests can be used:

(a) a determination of the degree of hydrolysis by Capillary Electrophoresis after 18 hours at 45° C. on a dispersed PVAc substrate, wherein the dispersed PVAc substrate is pre-pared by injecting 1.5 ml of 6% PVAc in methanol into 40 ml buffer, pH 6 or 8, and wherein the molecular weight of the PVAc is about 12800; or (b) a determination of the hydrolytic activity of the enzyme in question on at least one of the three following polymer preparations all comprising vinyl acetate monomer: (i) a PVAc homopolymer preparation, (ii) a vinyl acetate ethylene copolymer preparation, or (iii) a vinyl acetate tert-decanoic acid, ethenyl ester copolymer preparation. Hydrolytic activity on one, two or all three of these substrates shows that the enzyme is a "lipolytic" enzyme as defined herein.

For the purpose of test (a) above: If the degree of hydrolysis determined according to Example 8 herein is at least 0.1, the enzyme in question qualifies as a lipolytic enzyme for use according to the invention. The expression a PVAc molecular weight of about 12800 means average molecular weight by Gel Permeation Chromatography (GPC). In this context, "about 12800" means of an average molecular weight of between 10000 and 20000. A buffer pH value of 6 or 8 can be either pH 6 or pH 8. Examples of suitable buffers are 5 mM Hepes buffer (pH 8), and 5 mM MES (pH 6). In particular embodiments, the degree of hydrolysis is at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, or at least 2.0.

Surprisingly, a relatively small degree of hydrolysis seems to be required in order to reduce the stickiness of the stickies. In particular embodiments, the degree of hydrolysis is below 10%, or below 9%, or below 8%, or below 7%, or below 6%, or below 5%, or below 4%. In further particular embodiments, the degree of hydrolysis is within any range which can be derived from the above lower and upper values.

For the testing purposes according to (b) above, the polymer substrate is emulsified, and the reaction conditions such as pH, temperature and incubation time are selected paying due regard to the characteristics of the enzyme in question.

Examples of reaction temperatures are: 10, 20, 30, 35, 37, 40, 45, 50, 55, 60, 65, 70, 75, 80, 85, 90, 95 or 100° C.

Examples of reaction pH values are: pH 2, 3, 4, 5, 6, 7, 8, 9, 10, 11 or pH 12.

Examples of reaction times are: 30 seconds, 1 minute, 2, 3, 4, 5, 10, 20, 30, 60, 90, 120 or 180 minutes.

In a first particular embodiment the enzyme may have, preferably has, a hydrolytic activity at 35° C., pH 8 for 4 min with a 5% (w/v) poly(vinyl acetate) (PVAc) homopolymer preparation as substrate in an emulsion consisting of 50 mM NaCl, 0.5 mM $KH_2PO_4$, 9% (v/v) Glycerol and 0.1% (w/v) Gum Arabicum. In a particular embodiment hereof, the poly (vinyl acetate) homopolymer preparation (also designated PVAc homopolymer) is a homopolymer PVAc dispersion glue having a dry matter content in the range of 46 to 50%, and a viscosity in the range of 5800 to 7200 mPa·s (Brookfield, 20° C.). A preferred substrate is the product GLUDAN™ 150-6.500 available from the company GLUDAN A/S, Vesterlundvej 5-7, DK-2730 Herlev, Denmark (as used in Example 1 herein). In this first embodiment, the hydrolytic activity may be referred to as "PVAc hydrolytic activity."

In a second particular embodiment the enzyme has a hydrolytic activity at 35° C., pH 7 for 4 min with a 5% (w/v) vinyl acetate ethylene copolymer preparation as substrate in an emulsion consisting of 50 mM NaCl, 0.5 mM $KH_2PO_4$, 9% (v/v) Glycerol and 0.1% (w/v) Gum Arabicum. In a particular embodiment hereof, the vinyl acetate ethylene copolymer is a PVAc ethylene copolymer dispersion glue having a total solid content of 56 to 60%, and a viscosity of 6000 to 7000 mPa·s (Brookfield, 20° C.). A preferred substrate is the product GLUDAN™ 534-6.500 available from the company GLUDAN A/S, Vesterlundvej 5-7, DK-2730 Herlev, Denmark (as used in Example 2 herein).

In a third particular embodiment the enzyme has a hydrolytic activity at 35° C., pH 7 for 4 min with a 5% (w/v) vinyl acetate tert-decanoic acid, ethenyl ester copolymer preparation as substrate in an emulsion consisting of 50 mM NaCl, 0.5 mM $KH_2PO_4$, 9% (v/v) Glycerol and 0.1% (w/v) Gum Arabicum. In a particular embodiment hereof, the vinyl acetate tert-decanoic acid, ethenyl ester copolymer preparation is a vinyl acetate-Veova copolymer dispersion glue having a total solid content of 55+/−1%, and a viscosity of 1000 to 4000 cP (Brookfield, 23° C.). A preferred substrate is the product NOREMUL™ VW 1501 available from the company CHEMARK ApS, Noerregade 10A, 2. t.v., DK-4600 Koege, Denmark (as used in Example 3 herein). For the viscosity determinations, a suitable viscometer is of the type Brookfield LVF. Spindle no. 3 may be used at a speed of 60 rpm.

Under these conditions the hydrolytic activity (e.g. the PVAc hydrolytic activity) of a lipolytic enzyme is determined by adding 200 micro-liter of the lipolytic enzyme, dissolved in de-ionised water corresponding to $A_{280}$=0.15, to 15 ml of substrate emulsion, and one unit of hydrolytic activity (e.g. PVAc hydrolytic activity) is defined as the release of 1 micromole of acetate measured by a pH-stat. Typically, $A_{280}$=0.15 corresponds to about 0.10-0.40 mg enzyme protein/ml, depending on the extinction coefficient for the enzyme in question. For most of the enzymes used in the examples $A_{280=0.15}$ may correspond to about 0.20 to about 0.30 mg enzyme protein/ml, for example 0.25 mg enzyme protein/ml. In a particular embodiment, the amount of enzyme protein used in the assays (i.e. contained in the 200 micro-liter which is added to 15 ml of substrate emulsion) is about 40 to about 60, or about 45 to about 55, or about 50 micro-gram enzyme protein.

In a particular embodiment, the lipolytic enzyme may have, preferably has, a PVAc hydrolytic activity higher than 0.2 units, particularly 0.4 units or more particularly 0.6 units.

In another particular embodiment, the lipolytic enzyme has a PVAC hydrolytic activity of at least 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.2, 2.4, 2.6, 2.8, 3.0, 3.2, 3.4, 3.6, 3.8, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, or at least 13.5 units, per ml of the lipolytic enzyme solution having $A_{280}$ of 0.15.

In a further particular embodiment, the lipolytic enzyme has a hydrolytic activity on the vinyl acetate ethylene copolymer substrate of at least at least 0.2, 0.3, 0.4, 0.5, 0.6, 0.7. 0.8, 0.9, 1.0, 1.1, or at least 1.2 units/ml enzyme solution having an $A_{280}$ of 0.15.

In a still further particular embodiment, the lipolytic enzyme has a hydrolytic activity on the vinyl acetate tert-decanoic acid, ethenyl ester copolymer substrate of at least 0.2, 0.3, 0.4, 0.5, 0.6, 0.7. 0.8, 0.9, 1.0, 1.1, 1.2, 1.3, 1.4, 1.5, 1.6, 1.7. 1.8, 1.9, 2.0, or at least 2.1 units/ml enzyme solution having an $A_{280}$ of 0.15.

In various other embodiments, the lipolytic enzyme:
(iv) is active in the presence of LAS ("active" means, that the activity (measured in units/ml) in either of the assays (i)-(iii), adding 50 or 200 ppm LAS into the reaction, is at least 50% as compared to the activity in a control experiment without addition of LAS); in further particular embodiments the activity is at least 55, 60, 65, 70, 75, 80, 85, 90, 95, 100, 105, 110, 120 or at least 130% as compared to the control;
(v) is stable in the presence of LAS ("stable" means, that the residual activity (measured in units/ml) using either of the assays (i)-(iii), after pre-incubation of the enzyme ($A_{280=0.15}$) for 1, 2 or 3 hours, at pH 6 or 8, and a temperature of 45° C., in 50 or 200 ppm LAS (rest buffer pH 6 or 8), is at least 55, 60, 65, 70, 75, 80, 85, 90, 95, 100, 105, 110, 120 or at least 130% as compared to the control);
(v) shows a higher turbidity than the control after 20 minutes at 35, 45 or 55° C. and pH=8 (using 5 mM Hepes buffer), on a PVAC substrate, wherein the substrate is prepared by injection of 0.15 ml 2% w/v PVAc (Mw≈113000) in MeOH solution into 30 ml buffer (see Tables 4-6);
(v) is tolerant to hydrogen peroxide, viz. that substantially the same turbidity/enzyme dosage profile is obtained with and without addition of 15 ppm hydrogen peroxide (see Table 9); and/or
(vi) is tolerant to LAS, viz. substantially the same turbidity is obtained after 20 minutes, pH 7; 45° C. with 50 and 200 ppm LAS (see Table 11).

In a particular embodiment the lipolytic enzyme is well-defined, meaning that only one major enzyme component is present. In the alternative, the term well-defined means that only one major lipolytic enzyme component is present. Such well-defined, or purified, or highly purified, lipolytic enzymes can be obtained as is known in the art and/or described in publications relating to the specific enzyme in question. Fractionation of a well-defined enzyme on an appropriate Size-exclusion column reveals only one major enzyme component which is the lipolytic enzyme in question; or, in the alternative, reveals only one major lipolytic enzyme component, which is the lipolytic enzyme in question.

For a peak to qualify as a major peak, the area of the peak should correspond to at least 50, or 55, or 60, or 65, or 70, or 75, or 80, or 85, or 90, or 92, or 94, or 96, or at least 98% of the total peak area/total lipolytic peak area.

The skilled worker will know how to select an appropriate Size-exclusion chromatography column. He might start by fractionating the preparation on e.g. a HiLoad26/60 Superdex75 pg column available from Amersham Biosciences UK Limited, Amersham Place, Little Chalfont, Buckinghamshire HP7 9NA, UK. If the peaks would not be clearly separated he would try different columns (e.g. with an amended column particle size and/or column length), and/or he would amend the sample volume. See Example 11 herein for further details.

In a further particular embodiment, the lipolytic enzyme is desalted, i.e. substantially free from low molecular weight materials such as salts. Gel filtration chromatography is a suitable desalting technique. A preferred column material is Sephadex G-25, ensuring group separations of proteins/peptides larger than Mr 5000 from molecules with a Mr less than 1000. Mr designates relative molecular mass (molecular weight), and the units are in Dalton. Suitable columns are PD-10 columns available e.g. from Amersham, loaded with Sephadex G-25 M, or NAP5 columns. The standard procedure prescribed by the supplier is used, and desalted water (MilliQ) is used for equilibration and elution.

For determining lipolytic activity as described above, a well-defined and/or desalted lipolytic enzyme preparation is preferably used. Preferably the enzyme preparation is well-defined and desalted. As described in the Materials & Methods section herein, for carrying out the lipolytic activity test, the enzyme preparation is first diluted to $A_{280}$ of 0.15.

Examples of lipolytic enzymes as defined above are typically found amongst enzymes classified in EC 3.1.1 Carboxylic Ester Hydrolases according to Enzyme Nomenclature (available at http://www.chem.qmw.ac.uk/iubmb/enzyme, or from Enzyme Nomenclature 1992 (Academic Press, San Diego, Calif., with Supplement 1 (1993), Supplement 2 (1994), Supplement 3 (1995), Supplement 4 (1997) and Supplement 5 (in Eur. J. Biochem. 1994, 223, 1-5; Eur. J. Biochem. 1995, 232, 1-6; Eur. J. Biochem. 1996, 237, 1-5; Eur. J. Biochem. 1997, 250; 1-6, and Eur. J. Biochem. 1999, 264, 610-650; respectively), which are enzymes capable of hydrolysing carboxylic ester bonds. The lipolytic enzyme may have substrate specificity with an activity such as EC 3.1.1.3 triacylglycerol lipase or EC 3.1.1.74 cutinase.

The cutinase may be derived from a fungus. Particularly, the cutinase may be derived from a strain of *Humicola*, particularly *H. insolens*, more particularly *H. insolens* strain DSM1800 (U.S. Pat. No. 5,827,719) or from a strain of Fusarium, e.g. *F. roseum culmorum*, or particularly *F. solani pisi* (WO 90/09446; WO 94/14964, WO 94/03578). The fungal cutinase may also be derived from a strain of *Rhizoctonia*, e.g. *R. solani*, or a strain of *Alternaria*, e.g. *A. brassicicola* (WO 94/03578). The lipolytic enzyme may also be a variant of a parent cutinase such as those described in WO 00/34450, or WO 01/92502.

SEQ ID NO:1 is the amino acid sequence of the *Humicola insolens* cutinase (corresponding to the mature part of SEQ ID NO:2 of U.S. Pat. No. 5,827,719), and SEQ ID NO:2 is the amino acid sequence of the *Fusarium solani pisi* according to FIG. 1D of WO 94/14964.

Another example is a lipase as classified by EC 3.1.1.3. More particularly, a lipase derived from *Pseudomonas*, such as *P. putida* ATCC 53552 (WO 88/09367; WO 89/09263), *P. cepacia* (U.S. Pat. No. 4,876,024), *P. mendocina* (U.S. Pat. No. 5,389,536) *P. alcaligenes* (U.S. Pat. No. 6,313,283), *P. gladioli* (EP 205208; EP 206390) or *Pseudomonas* sp. (U.S. Pat. No. 5,942,431). The lipolytic enzyme may also be a variant of a parent lipase such as those described in e.g. EP 0943678, U.S. Pat. No. 5,352,594 or WO 94/25578.

Another example is lipase B from *Candida antarctica* (U.S. Pat. No. 5,273,898) or an enzyme having an amino acid sequence, which has at least 60%, particularly 65%, more particularly 70%, or 75%, or 80%, or 85%, or 90%, or 92%, or 95%, or 97%, or at least 99% homology to lipase B from *Candida antarctica* (U.S. Pat. No. 5,273,898) such as a lipase from *Hyphozyma* (U.S. Pat. No. 5,856,163). This lipase has SEQ ID NO:3.

Another example is an enzyme having an amino acid sequence, which may have at least 70% homology, particularly 75%, or 80%, 90%, 92%, 95%, 97%, or at least 99% homology to SEQ ID NO:1 or SEQ ID NO:2.

In the context of the present invention homology is determined as the degree of similarity between two sequences indicating a derivation of the first sequence from the second. The similarity is determined by means of the computer program GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-453, using GAP with the following settings for polypeptide sequence comparison: GAP creation penalty of 3.0 and GAP extension penalty of 0.1. In a particular embodiment, the homology is determined as the degree of identity using the program and the settings specified above, in which case for the present purposes "homology" may be replaced by "identity," and "homologous" with "identical."

Paper Manufacturing Process

The present invention relates to a method for making paper comprising: a) preparing a pulp from a material comprising recycled paper; b) treating the pulp with a lipolytic enzyme, which is able to hydrolyze a polymer comprising vinyl acetate monomer; c) making paper from the treated pulp.

For the purposes of the present invention, any type of paper making process is relevant and/or any paper making pulp can be applied, as long as it comprises recycled paper. In particular embodiments, the amount of pulp based on recycled paper relative to the total amount of pulp is at least 2%, or at least 4%, or at least 6%, or at least 8%, or at least 10%, or at least 15, 20, 25, 30, 35, 40, 45, 50, 55, 60, 65, 70, 75, 80, 85, 90 or at least 95%. In further particular embodiments, the amount of pulp based on recycled paper relative to the total amount of pulp is not higher than 25%, or not higher than 30%, or 35, 40, 45, 50, 55, 60, 65, 70, 75, 80, 85, 90, 95 or not higher than 98%. In still further particular embodiments, the amount of pulp based on recycled paper relative to the total amount of pulp lies within any interval which can be derived from the above upper and lower values. Dry weight is preferably used for determining the amount of pulp.

The part of the pulp which is not derived from recycled paper may be derived from mechanical pulping, chemical pulping, and any mixtures thereof such as chemi-mechanical pulping, thermo-mechanical pulping, chemi-thermo-mechanical pulping etc.

For preparing a pulp from a material comprising recycled (or waste) paper, also known as secondary fibres, the material is mixed, dispersed, or suspended in water. This is the process known as pulping. Thereby at least part of the ink and other contaminants such as glue, adhesives, coatings etc. is released from the fibres. A papermaking pulp often comprises both recycled paper and fresh so-called virgin pulp. The pulp may have a high (above 18%), medium (7-18%), or low (below 7%) consistency. In particular embodiments, the method and the use of the invention are operated at a high, a medium or a low pulp consistency.

The source of recycled fibre can be any of the grades of recycled furnishes known in the art or mixtures thereof, as well as mixtures of recycled fibres with virgin fibres. Major grades of recycled fibre furnishes are for instance MOW (mixed office waste), SOW (sorted office waste), ONP (old newsprint), WM (waste magazines) and OCC (old corrugated containers).

The lipolytic enzymes for use in the method and use of the invention are disclosed in the section herein headed "Lipolytic Enzymes."

The expression "treating the pulp" basically means adding the enzyme in question to the pulp. The treatment takes place at suitable conditions. The conditions of the treatment may be varied depending on particular paper manufacturing process parameters or requirements, and on the characteristics of the enzyme in question, such as pH-activity and -stability range, temperature activity and -stability range, rate of hydrolysis etc. Examples of treatment conditions are described in the section herein headed "Process Conditions." In particular embodiments, the conditions are suitable to reduce the amount of stickies, and/or to obtain a de-inking (see below).

Making paper from the treated pulp comprises forming the enzyme-treated fibres into paper or paperboard products.

Over and above steps a)-c) further, optional, steps may be included, for example one or more of the following steps:
d) de-inking, e.g. by pulping the fibres in the presence of an aqueous alkaline solution, optionally containing a peroxide compound, such as hydrogen peroxide;
e) separation of the fibres from the contaminants, e.g. by screening (coarse and/or fine);
f) centrifugal cleaning;
g) flotation, e.g. using one or more surfactants;
h) washing, e.g. using one or more surfactants;
i) dispersion; e.g. using one or more surfactants; and/or
j) inactivation of the enzymes, if required, e.g. by a heat treatment step.

Any number of these additional steps may be included, and the sequence need not be as indicated a-b-c-d-e-f-g-h-i-j. In a particular embodiment, step d) and/or j) are included. The lipolytic enzymes as defined herein may advantageously be used also in the de-inking step d).

The enzyme may be introduced prior to the pulping, during a pulping stage, during or before, preferably right before, a stock preparation stage, or after a flotation or a de-inking stage. In particular embodiments, it is introduced in the paper machine headbox, or in the paper machine white water.

The process may be a closed loop process (at least a part of the water being re-used, e.g. at least 10%, 15, 20, 25, 30, 40, 50, 60, 70, or at least 80% of the water being re-used (vol/vol)).

In further particular embodiments of the method and the use of the invention, the enzyme serves the purpose of controlling stickies. Controlling stickies means that the amount of stickies is reduced as compared to a control not treated with enzymes. In preferred embodiments, the amount of stickies in a sample treated with the enzyme in question is maximum 95%, or 90%, or 80%, or 75%, or 70%, or 60%, or 50%, or 40%, or 30%, or maximum 20% (w/w), as compared to the control. Any of the methods disclosed in Examples 1-6 of WO01/98579 may be used for this determination.

In still further embodiments of the method and the use of the invention, the enzyme serves de-inking purposes. The enzyme can be applied to de-ink recycled paper with printing made by any printing method, e.g. off set printing, gravure printing, and letterpress printing. The effect of the enzyme is to improve the whiteness or brightness of and/or reduce the amount of ink in the resulting paper. This can be measured as generally known in the art, e.g. as disclosed in JP patent no. 96014078.

Glycerides present in the virgin pulp tend to agglomerate with a polymer comprising vinyl acetate monomer from the recycled paper pulp in the stickies. Thus in another example the method of the present invention may comprise a lipolytic enzyme capable of hydrolyzing a polymer comprising vinyl acetate monomer and a lipase capable of hydrolyzing the ester bonds in a glyceride, such as those classified by EC 3.1.1.3.

Accordingly, the method and the use according the invention may be carried out with a combination of enzymes in order to make the enzymatic process effective against a broader range of contaminants, such as proteinaceous impurities, starch-containing impurities, triglyceride containing impurities as well as contaminants containing hemi-celluloses and pectins. The lipolytic enzymes for use according to the invention can thus be combined with at least one additional enzyme, selected from amongst proteases, amylases, pullulanases, lipases, hemicellulases, endoglucanases, cutinases, and pectinases. These enzymes may be wild-type enzymes, or mutants or variants thereof having the relevant enzyme activity, i.e. catalyzing at least one of the reactions indicated at the following web-site for the relevant enzyme class: http://www.expasy.ch/enzyme/.

Examples of suitable proteases are the ALCALASE, ESPERASE, SAVINASE, NEUTRASE and DURAZYM proteases. Other preferred serine-proteases are proteases from *Nocardiopsis, Aspergillus, Rhizopus, Bacillus alcalophilus, B. cereus, B. natto, B. vulgatus, B. mycoide*, and subtilisins from *Bacillus*, especially proteases from the species *Nocardiopsis* sp. and *Nocardiopsis dassonvillei* such as those disclosed in WO 88/03947, especially proteases from the species *Nocardiopsis* sp., NRRL 18262, and *Nocardiopsis dassonvillei*, NRRL 18133. Yet other preferred proteases are the serine proteases from mutants of *Bacillus subtilis*, e.g. those disclosed in WO 91/00345 and EP 415296. Examples of suitable amylases are the BAN, AQUAZYM, TERMAMYL, and AQUAZYM Ultra amylases. An example of a lipase is the RESINASE A2X lipase. An example of a hemicellulase is the PULPZYME HC hemicellulase. Examples of endoglucanases are the NOVOZYM 613, 342, and 476 enzyme products. An example of a pectinase is the NOVOZYME 863 enzyme product. An example of a pullulanase is the PROMOZYM pullulanase. The enzymes written in capitals are commercial enzymes available from Novozymes A/S, Krogshoejvej 36, DK-2880 Bagsvaerd, Denmark.

Particularly the method of the present invention may be used on a polymer comprising vinyl acetate monomer present in and/or on paper. More particularly, it may be used to hydrolyze a polymer comprising vinyl acetate monomer in a papermaking pulp of recycled paper to diminish the problem with stickies. Alternatively, it may be used to remove labels, such as mailing- and bottle-labels. In another example the method of the present invention may be for stickies control during recycling of paper. The method of the present invention may be carried out with stirring or mechanical agitation.

Process Conditions

For the method for making paper and the use in the manufacture of paper of at least one lipolytic enzyme as defined herein, the lipolytic enzyme in question need not be as pure as described above. First of all, it need not be a well-defined enzyme preparation. Secondly, the enzyme preparation may not be a desalted enzyme preparation.

In a particular embodiment, however, the enzyme preparation is well-defined. This is mainly because a well-defined preparation is advantageous, e.g. as regards consistency and reproducibility of results.

The process conditions will be a function of the enzyme(s) applied, the reaction time and the conditions given. Generally, the enzyme is dosed in a sufficient amount to control the stickies present in the paper pulp. However, it is contemplated that the enzyme(s) may be dosed in total amount from 0.1 to 5000 units per gram of polymer comprising vinyl acetate monomer, particularly from 0.5 to 1000 units per gram of polymer comprising vinyl acetate monomer, more particularly from 1 to 500 units per gram of polymer comprising vinyl acetate monomer wherein one unit refers to the PVAc hydrolytic activity as described above.

In particular embodiments, the dosage of the lipolytic enzyme is from about 100 to about 100.000 units per ton of paper pulp. In particular embodiments, these units refer to (i) PVAc hydrolytic activity; (ii) activity on vinyl acetate ethylene copolymer; or (iii) activity on vinyl acetate tert-decanoic acid, ethenyl ester copolymer (using the methods specified herein). In a preferred embodiment, the units refer to (i) PVAc hydrolytic activity. Further examples of particular dosage ranges (all "from about" and "to about," and in units per ton paper pulp) are the following: 200-100.000; 400-100.000; 600-100.000; 800-100.000; 1000-100.000; 1200-100.000; 1500-100.000; 2000-100.000; 100-90.000; 100-80.000; 100-70.000; 100-60.000; 100-50.000; 100-40.000; 100-30.000; 100-20.000; 100-10.000; as well as any combination of the upper and lower values here indicated.

In other particular embodiments, the dosage of the lipolytic enzyme is from about 0.1 mg enzyme protein to about 100.000 mg enzyme protein per ton of paper pulp. Enzyme protein may be determined as described in Example 11 herein. Further examples of particular dosage ranges (all "from about" and "to about," and in units per ton paper pulp) are the following: 0.5-100.000; 1-100.000; 5-100.000; 10-100.000; 20-100.000; 40-100.000; 60-100.000; 80-100.000; 100-100.000; 150-100.000; 200-100.000; 500-100.000; 0.1-90.000; 0.1-80.000; 0.1-70.000; 0.1-60.000; 0.1-50.000; 0.1-40.000; 0.1-30.000; 0.1-20.000; 0.1-10.000; 0.1-8.000; 0.1-6.000; 0.1-4.000; 0.1-2.000; 0.1-1.000; as well as any combination of the upper and lower values here indicated.

The enzymatic treatment may be carried out at a temperature of from about 10 to about 100° C. Further examples of temperature ranges (all "from about" and "to about") are the following: 20-100, 30-100, 35-100, 37-100, 40-100, 50-100, 60-100, 70-100, 10-90, 10-80, 10-70, 10-60, and 30-60° C., as well as any combination of the upper and lower values here indicated.

The enzymatic treatment may be carried out at a pH of from about 2 to about 12. Further examples of pH ranges (all "from about" and "to about") are the following: 3-12, 412, 5-12, 6-12, 7-12, 8-12, 9-12, 2-11, 2-10, 2-9, 2-8, 4-10, 5-8 as well as any combination of the upper and lower values here indicated.

A suitable duration of the enzymatic treatment may be in the range from a few seconds to several hours, e.g. from about 30 seconds to about 48 hours, or from about 1 minute to about 24 hours, or from about 1 minute to about 18 hours, or from about 1 minute to about 12 hours, or from about 1 minute to 5 hours, or from about 1 minute to about 2 hours, or from about 1 minute to about 1 hour, or from about 1 minute to about 30 minutes.

Additives

Various additives over and above the lipolytic enzyme can be used in the process or use of the invention. For example, talc, clay and other inorganic particles may be used to render the stickies less tacky, and dispersants, surfactants, polymers, and solvents may be used to reduce the size of the stickies and/or keep them dispersed or suspended.

Surfactants and/or dispersants are often present in and/or added to a papermaking pulp. Thus the method of the present invention may be carried out in the presence of an anionic, non-ionic, cationic and/or zwitterionic surfactant and/or dispersant conventionally used in a papermaking pulp. An enzyme capable of hydrolyzing a polymer comprising vinyl acetate monomer may be an enzyme, which is active and stable in the presence of an anionic, non-ionic, cationic and/or zwitterionic surfactant and/or dispersant conventionally used in a papermaking pulp or during washing of textiles.

Examples of anionic surfactants are carboxylates, sulphates, sulphonates or phosphates of alkyl, substituted alkyl or aryl. Examples of non-ionic surfactants are polyoxyethylene compounds, such as alcohol ethoxylates, propoxylates or mixed ethoxy-/propoxylates, polyglycerols and other polyols, as well as certain block-copolymers. Examples of cationic surfactants are water-soluble cationic polymers, such as quartenary ammonium sulphates and certain amines, e.g.

epichlorohydrin/dimethylamine polymers (EPI-DMA) and cross-linked solutions thereof, polydiallyl dimethyl ammonium chloride (DADMAC), DADMAC/Acrylamide copolymers, and ionene polymers, such as those disclosed in U.S. Pat. Nos. 5,681,862; and 5,575,993. Examples of zwitterionic or amphoteric surfactants are betains, glycinates, amino propionates, imino propionates and various imidazolin-derivatives. Also the polymers disclosed in U.S. Pat. No. 5,256,252 may be used.

Also according to the invention, surfactants such as the above, including any combination thereof may be used in a paper making process together with at least one lipolytic enzyme as defined herein, and included in a composition together with such enzyme. The amount of each surfactant in such composition may amount to from about 8 to about 40% (w/w) of the composition. In particular embodiments the amount of each surfactant is from about 10 to about 38, or from about 12 to about 36, or from about 14 to about 34, or from about 16 to about 34, or from about 18 to about 34, or from about 20 to about 34, or from about 22 to about 34, or from about 24 to about 34, or from about 26 to about 34, or from about 28 to about 32% (w/w).

In another particular embodiment, each of the above ranges refers to the total amount of surfactants.

The compositions are preferably additives for the manufacture of paper. In a particular embodiment, they are non-build compositions, i.e. they do not contain builders. Examples of builders are certain phosphates, zeolites etc. conventionally used for detergent compositions.

The compositions may comprise at least one additional enzyme selected from the following group of enzymes: Proteases, amylases, pullulanases, lipases, hemicellulases, endoglucanases, cutinases, and pectinases; as well as any combination thereof.

The compositions may be stabilized using the formulations described in e.g. U.S. Pat. Nos. 5,356,800; 5,780,283.

The invention also relates to:
(I) a method for hydrolyzing a polymer comprising vinyl acetate monomer by treating with a cutinase; a method according to the above wherein the cutinase is derived from a fungus; a method according to the above wherein the cutinase is derived from *Humicola insolens* or *Fusanum solani pisi*; a method for hydrolyzing a polymer comprising vinyl acetate monomer by treating with a lipase derived from *Pseudomonas*; a method for hydrolyzing a polymer comprising vinyl acetate monomer by treating with a lipase having an amino acid sequence, which has at least 60% homology to lipase B from *Candida antarctica* SEQ ID NO. 3; a method for hydrolyzing a polymer comprising vinyl acetate monomer by treating with a lipolytic enzyme having an amino acid sequence, which has at least 70% homology to SEQ ID NO. 1 or SEQ ID NO. 2;
(II) a method for hydrolyzing a polymer comprising vinyl acetate monomer treating the polymer with an enzyme, which has a hydrolytic activity at 35° C., pH 8 for 4 min with 5% (w/v) poly (vinyl acetate) (PVAc) homopolymer as substrate in a emulsion consisting of 50 mM NaCl, 0.5 mM $KH_2PO_4$, 9% (v/v) Glycerol and 0.1% (w/v) Gum Arabicum; and
(III) use of an enzyme in the manufacture of paper, which enzyme has
   a) a degree of hydrolysis by Capillary Electrophoresis of at least 0.1 after 18 hours at 45° C. on a dispersed PVAc substrate, wherein the dispersed PVAc substrate is prepared by injecting 1.5 ml of 6% PVAc in methanol into 40 ml buffer pH 6 or 8, and wherein the molecular weight of the PVAc is about 12800; and/or
   b) a hydrolytic activity at 35° C. for 4 min with a 5% (w/v) polymer preparation comprising vinyl acetate as substrate in an emulsion consisting of 50 mM NaCl, 0.5 mM $KH_2PO_4$, 9% (v/v) Glycerol and 0.1% (w/v) Gum Arabicum, wherein the polymer is:
      (i) a PVAc homopolymer preparation and the reaction pH is 8;
      (ii) a vinyl acetate ethylene copolymer preparation, and the reaction pH is 7; and/or
      (iii) a vinyl acetate tert-decanoic acid, ethenyl ester copolymer preparation, and the reaction pH is 7;
as well as the use of above (III), wherein the hydrolytic activity under the conditions of (i) is higher than 0.2 units, preferably higher than 0.4 units, still more preferably higher than 0.6 units; wherein the enzyme has a PVAc hydrolytic activity of at least 0.7 units/ml; wherein the hydrolytic activity under the conditions of (ii) is at least 0.2 units/ml; wherein the hydrolytic activity under the conditions of (iii) is at least 0.2 units/ml; wherein for the determination of degree of hydrolysis according to a), and for the determination of hydrolytic activity according to any one of steps (i)-(iii), the enzyme is well-defined; wherein for the determination of degree of hydrolysis according to a), and for the determination of hydrolytic activity according to any one of steps (i)-(iii), the enzyme is desalted; wherein for the determination of hydrolytic activity according to any one of steps (i)-(iii), 200 micro-liter of an enzyme solution of $A_{280}$=0.15, or 50 microgram enzyme protein, is added to 15 ml of substrate emulsion; for stickies control and/or for the manufacture or paper prepared at least partly on the basis of recycled paper; wherein for the manufacture of paper the enzyme dosage is from 0.1 to 5000 units of PVAc hydrolytic activity per gram of polymer comprising vinyl acetate monomer; wherein the enzyme dosage per ton of paper pulp is: (i) from about 100 to about 100.000 units according to (i) of (III); or (ii) from about 0.1 to about 100.000 mg enzyme protein; wherein the enzyme is active and stable in the presence of LAS and/or hydrogen peroxide: further comprising the use of at least one additional enzyme, which additional enzyme is selected from the following group of enzymes: Proteases, amylases, pullulanases, lipases, hemicellulases, endoglucanases, cutinases, and pectinases; and/or further comprising the use of at least one anionic, non-ionic, cationic and/or zwitterionic surfactant and/or dispersant.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

Materials and Methods

Enzymes

A) Cutinase from *Humicola insolens* according to U.S. Pat. No. 5,827,719.
B) Thermostable variant of A).
C) Thermostable variant of A) according to WO 00/34450.
D) Cutinase from *Fusarium solani pisi* according to WO 94/14964.
E) Lipase B from *Candida antarctica* according to U.S. Pat. No. 5,273,898.

F) Lipase from *Pseudomonas cepacia* according to U.S. Pat. No. 4,876,024.
G) Lipase from *Pseudomonas* sp. according to U.S. Pat. No. 5,942,431.
H) Phospholipase from Porcine Pancreas.
I) NOVOCOR ADL lipase.
J) RESINASE A 2X lipase.
K) Variant of J) with lipase and phospholipase activity according to WO 00/32758.
L) Ferulic acid esterase from *Aspergillus niger*.

The NOVOCOR ADL and RESINASE A 2X lipases are commercial enzyme products available from Novozymes A/S, Krogshoejvej 36, DK-2880 Bagsvaerd, Denmark.

The variants of the *Humicola insolens* cutinase shown in the below Table A were pre-pared as described in WO 00/34450 and WO 01/92502 and tested for lipolytic activity as described in the following. The test results for two of these variants are indicated in the examples as B) and C).

Reagents/Substrates
0.025 M NaOH
5 mM MES Buffer pH 86.5
0.98 g MES 2-[N-Morpholino]Ethanesulfonic Acid Hydrate
0.44 g $CaCl_2$, $2H_2O$
0.246 g $MgSO_4$, $7H_2O$
Milli Q water added up to 1 liter
pH adjusted with weak NaOH or HCl
5 mM Hepes Buffer PH 7-9
1.19 g Hepes (N-[2-Hydroxyethyl]piperazine-N-[2-Ethane-sulfonic Acid])
0.44 g $CaCl_2$, $2H_2O$
0.246 g $MgSO_4$, $7H_2O$
Milli Q water added up to 1 liter
pH adjusted with weak NaOH or $HC_{1-6}$
6% w/v Poly (vinyl acetate) PVAc in MeOH Solution

TABLE A

R51P
E6N/Q + L138I
A14P + E47K
E47K
E179N/Q
E6N/Q + E47K+R51P
A14P + E47K + E179N/Q
E47K + E179N/Q
E47K + D63N
E6N/Q + E10N/Q + A14P + E47K + R51P + E179N/Q
E6N/Q + A14P + E47K + R51P + E179N/Q
E6Q + A14P + E47K + R51P + E179Q
Q1P + L2V + S11C + N15T + F24Y + L46I + E47K
E6Q + A14P + E47K + R51P + E179Q + S48E + A88H + N91H + R189V
E6Q + A14P + E47K + R51P + E179Q + N44D + A130V
E6Q + A14P + E47K + R51P + E179Q + Q1C + L2V + G120D
E6Q + A14P + E47K + R51P + E179Q + A88L + R189A
E6Q + A14P + E47K + R51P + E179Q + S48E + L66I + A88L + I169A + R189H
E6Q + A14P + E47K + R51P + E179Q + A88V + S116K + S119P + Q139R + I169V + R189V
E6Q + A14P + E47K + R51P + E179Q + A88V + R189A
E6Q + A14P + E47K + R51P + E179Q + S48K + A88H + I169G + R189H
E6Q + A14P + E47K + R51P + E179Q + Q1L + L2Q + A4V + S11T
E6Q + A14P + E47K + R51P + E179Q + T164S
E6Q + A14P + E47K + R51P + E179Q + L174F
E6Q + A14P + E47K + R51P + E179Q + H49Y
E6Q + A14P + E47K + R51P + E179Q + G8D + N15D + A16T
E6Q + A14P + E47K + R51P + E179Q + A130V
E6Q + A14P + E47K + R51P + E179Q + Q1C + L2V
E6Q + A14P + E47K + R51P + E179Q + G8D + N15D + S48E + A88H + N91H + A130V + R189V
E6Q + A14P + E47K + R51P + E179Q + G8D + N15D + T29M + S48E + A88H + N91H + A130V + R189V
E6Q + A14P + E47K + R51P + E179Q + G8D + N15D + T29I + S48E + A88H + N91H + A130V + R189V
E6Q + A14P + E47K + R51P + E179Q + G8D + N15D + T29C + S48E + A88H + N91H + A130V + R189V
E6Q + A14P + E47K + R51P + E179Q + G8D + N15D + S48E + A88H + N91H + A130V + L174F + I178V + R189V
E6Q + A14P + E47K + R51P + E179Q + G8D + N15D + S48E + A88H + N91H + A130V + T166M + I168F + R189V
E6Q + A14P + E47K + R51P + E179Q + G8D + N15D + S48E + A88H + N91H + A130V + T166I + L167P + R189V
E6Q + A14P + E47K + R51P + E179Q + G8D + N15D + V38H + S48E + A88H + N91H + A130V + I169T + R189V
E6Q + A14P + E47K + R51P + E179Q + G8D + N15D + V38H + S48E + A88H + N91H + A130V + R189V
E6Q + A14P + E47K + R51P + E179Q + G8D + N15D + T29M + S48E + A88H + N91H + A130V + T166I + L167P + R189V 6 g PVAC Mw≈12800 (GPC) (Aldrich Chemical Company. Inc. Cat. No. 43,043-9)
dissolved in approx. 80 ml MeOH at approx. 50° C. Let cool. MeOH is added up to 100 ml
2% w/v Poly (vinyl acetate) PVAc in MeOH Solution
2 g PVAC Mw≈1113000 (Aldrich Chemical Company. Inc. Cat. No. 18.948-0)
dissolved in approx. 80 ml MeOH at approx. 50° C. Let cool. MeOH is added up to 100 ml
LAS (LAS Nansa 1169 A, dodecyl benzene sulphonate sodium salt, Albright & Wilson).
Emulsion Reagent
17.9 g NaCl
0.41 g $KH_2PO_4$
540 ml Glycerol
6.0 g Gum Arabicum
NaCl, $KH_2PO_4$, Glycerol and 400 ml DI water are mixed before Gum Arabicum is added under strong stirring. Stirring is continued until it is completely dissolved. DI water is added up to 1 l.
Substrate Emulsion for Examples 1-3
15 g PVAc homo- or copolymer (Gludan, Denmark) (example 1, and examples 2-3, respectively)
50 ml Emulsion reagent
235 ml DI water
The solution is stirred for about 30 min until all the substrate is dissolved.
Equipment
Titrator: Radiometer Titralab (Vit 90)
Electrode: Orion 8103 Ross—Semi micro Combination pH electrode, glass body.
Turbidimeter: HACH Turbidimeter 2100AN with a USEPA filter Cat. 30312-00, including a special glass (sample cells cat. No. 2084900) fitting the apparatus.
Water bath: Water bath including a magnetic stirrer (oblong stir bars, 15 mm)
Water bath: Water bath with temperature control.
Filters: 0.22 micro-m filters (Millex-GV single use filters by Millipore)
Capillary Electrophoresis:
Hewlett Packard 3D CE with Chemstation software
Agilent buffer: Agilent Basic Anion Buffer for HPCE, Part. No. 5064-8209
Agilent capillar:
Agilent, Fused silica, CE ext. Light path cap. Inner diameter 50 micro-m, effective length 104 cm, total length 112.5 cm, Part. no. G1600-64232
Tensiometer: KSV Sigma 70 Model 6000, equipped with a platinum Wilhelmy plate (dim. 10 mm×20 mm), temperature regulation and stirring of solution

EXAMPLES

Examples 1-3

Polymer preparations comprising vinyl acetate monomer is hydrolysed at a constant pH under release of acetate by an enzyme. The release of acetate as a function of time is measured by neutralization with base by pH-stat titration.

The Titrator (see Equipment) is turned on, the water bath is set to 35° C. and the electrode is calibrated using regular calibration buffers. Fifteen ml of substrate emulsion is added to each beaker and allowed to heat for 3 min to obtain the right temperature (the substrate should be stirred at all times prior to use to avoid precipitation). The pH is adjusted with a freshly made diluted NaOH solution (25 mM). Enzyme solutions (in de-ionised water) are prepared on the basis of highly purified and desalted enzymes corresponding to Enzymes A)-L). The solutions correspond to an absorbance of $A_{280}$=0.15, and 200 micro-liter thereof is added to the substrate emulsion and the titration is begun, using 25 mM NaOH. After 4 min the titration is stopped. The average consumption in ml per minute of NaOH is calculated for the period 2-4 minutes, and this value is used for the below unit calculation.

1 unit enzyme is defined as the amount of enzyme that releases 1 micro mole titratable acetate per min by hydrolysis of the substrate under the given conditions. Units/ml as indicated in the below tables refers to ml of the enzyme solution of $A_{280}$=0.15.

Example 1

Hydrolysis of PVAc Homopolymer

The ability of different lipolytic enzymes to degrade a PVAc homopolymer preparation was measured as described above. Before addition of the enzyme to the substrate emulsion, pH was adjusted to 8. The results are shown in table 1.

TABLE 1

| Type of enzyme | Enzyme | PVAc hydrolytic activity (U/ml) |
|---|---|---|
| Cutinase | A) *H. insolens* | 2.9 |
|  | B) Thermostable variant of A) | 1.8 |
|  | C) Thermostable variant of A) | 3.0 |
|  | D) *F. solani pisi* | 1.0 |
| Lipase B from *C. antarctica* | E) *C. antarctica* | 13.6 |
| Lipase from *Pseudomonas* | F) *P. cepacia* | 0.6 |
|  | G) *P.* sp. | 0.2 |
| Other lipases | H) Phospholipase from Porcine Pancreas | 0 |
|  | I) NOVOCOR ADL lipase | 0 |
|  | J) RESINASE A 2X lipase | 0 |
|  | K) Variant of J) | 0 |
|  | L) Ferulic acid esterase from *A. niger* | 0 |

Example 2

Hydrolysis of a Vinyl Acetate Copolymer

The ability of lipolytic enzymes to degrade a vinyl acetate copolymer preparation consisting of vinyl acetate and ethylene was measured as described above. Before addition of the enzyme to the substrate emulsion, pH was adjusted to 7. The results are shown in table 2.

TABLE 2

| Type of enzyme | Enzyme | Hydrolytic activity (U/ml) |
|---|---|---|
| Cutinase | A) *H. insolens* | 1.2 |
|  | B) Thermostable variant of A) | 0.6 |
|  | C) Thermostable variant of A) | 0.5 |
| Lipase B from *C. antarctica* | G) *C. antarctica* | 0.3 |
| Other lipases | J) RESINASE A 2X lipase | 0 |

Example 3

Hydrolysis of a Latex-Based Vinyl Acetate Copolymer

The ability of lipolytic enzymes to degrade a vinyl acetate copolymer preparation consisting of vinyl acetate and tert-Decanoic acid, ethenyl ester was measured as described above. Before addition of the enzyme to the substrate emulsion, pH was adjusted to 7. The results are shown in table 3.

TABLE 3

| Type of enzyme | Enzyme | Hydrolytic activity (U/ml) |
|---|---|---|
| Cutinase | A) *H. insolens* | 1.9 |
|  | B) Thermostable variant of A) | 1.9 |
|  | C) Thermostable variant of A) | 2.1 |
| Other lipases | J) RESINASE A 2X lipase | 0 |

Examples 4-10

In examples 4-10 pure Poly (vinyl acetate), abbreviated PVAc, is used as a substrate. PVAc is not soluble in water but in methanol. When small amounts of PVAc solubilized in methanol is injected into water, the PVAc momentarily precipitates in extremely small particles, and the liquid becomes turbid. These particles tend to agglomerate into much bigger particles due to their stickiness, resulting in a decreased turbidity. With enzymes showing lipolytic activity (e.g. PVAc hydrolytic activity), this agglomeration can be prevented. Accordingly, the effect of a lipolytic enzyme is measured directly as the turbidity of the PVAc dispersion as a function of time. Turbidity is measured in NTU-units (Nephelometric Turbidity Units). A low number indicates that the sample is clear, and a high number that the sample is turbid (i.e. the enzyme works to decrease stickiness). In these examples, the enzyme dosage is given in ppm (w/w) enzyme protein.

Example 4

Ability to Agglomerate PVAc

Add a stir bar and 30 ml of buffer to the glass. Put the glass in the water bath, and await adjustment to the prescribed temperature. The speed of the magnetic stirrer is kept constant. Remove an amount of buffer corresponding to the volume of the enzyme solution to be added (to make sure the volume is constant). Add the enzyme. Inject 0.15 ml 2% w/v PVAC (Mw≈113000) in MeOH solution, and start the timer. After stirring for 10 seconds, the time=0 turbidity is determined. Measure the turbidity as a function of time.

The results using 10 ppm of enzyme B), at 35, 45 or 55° C., respectively, and pH=8 (using 5 mM Hepes buffer) are shown in below Tables 4-6, respectively.

TABLE 4

| Time (min) | Turbidity (NTU) Blank 35° C. | Turbidity (NTU) 10 ppm enzyme B) 35° C. |
|---|---|---|
| 0 | 118 |  |
| 1 | 110 |  |
| 2 | 97 |  |
| 3 | 87 |  |
| 4 | 80 |  |
| 8 | 31 |  |
| 0 |  | 134 |
| 1 |  | 126 |
| 2 |  | 120 |
| 3 |  | 117 |
| 4 |  | 115 |
| 5 |  | 113 |
| 6 |  | 113 |
| 13 |  | 109 |
| 18 |  | 107 |
| 37 |  | 106 |
| 60 |  | 105 |
| 120 |  | 97 |

TABLE 5

| Time (min) | Turbidity (NTU) Blank 45° C. | Turbidity (NTU) 10 ppm enzyme B) 45° C. |
|---|---|---|
| 0 | 107 |  |
| 1 | 104 |  |
| 2.5 | 81 |  |
| 4 | 71 |  |
| 6 | 59 |  |
| 8 | 49 |  |
| 10 | 37 |  |
| 12 | 32 |  |
| 13 | 29 |  |
| 0 |  | 118 |
| 1.5 |  | 112 |
| 4 |  | 108 |
| 7 |  | 106 |
| 10.5 |  | 105 |
| 53 |  | 103 |
| 60 |  | 103 |

TABLE 6

| Time (min) | Turbidity (NTU) Blank 55° C. | Turbidity (NTU) 10 ppm enzyme B) 55° C. |
|---|---|---|
| 0 | 101 |  |
| 1 | 98 |  |
| 3 | 77 |  |
| 5 | 67 |  |
| 7 | 60 |  |
| 9 | 53 |  |
| 11 | 49 |  |
| 13 | 44 |  |
| 15 | 40 |  |
| 17 | 37 |  |
| 20 | 33 |  |
| 22 | 31 |  |
| 0 |  | 135 |
| 2 |  | 132 |
| 3 |  | 132 |
| 6 |  | 132 |
| 11 |  | 130 |
| 13 |  | 130 |
| 20 |  | 129 |
| 75 |  | 125 |

Table 7 shows Dose-Response figures for two lipolytic enzymes at 45° C., pH=8 using 5 mM Hepes buffer. The turbidity was measured after 20 minutes. The figures are average of three experiments.

TABLE 7

| Enzyme dosage (ppm) | Turbidity (NTU) Enzyme B) | Turbidity (NTU) Enzyme C) |
|---|---|---|
| 0 | 11 | |
| 0.5 | 45 | |
| 1 | 57 | |
| 1.5 | 88 | |
| 2 | 91 | |
| 3.5 | 112 | |
| 5 | 115 | |
| 10 | 120 | |
| 0 | | 11 |
| 10 | | 43 |
| 50 | | 51 |

Table 8 shows the effect of a lipolytic enzyme versus pH (45° C.; turbidity after 20 minutes; enzyme dosage 10 ppm of enzyme B). The figures are average of three experiments.

TABLE 8

| pH | Turbidity (NTU) Blank | Turbidity (NTU) 10 ppm enzyme B) |
|---|---|---|
| 6 | 8.6 | 44.3 |
| 6.5 | 10.5 | 118 |
| 7 | 10.5 | 114.7 |
| 8 | 12.3 | 130 |
| 9 | 19 | 129 |
| 10 | 12.6 | 127.5 |

Example 5

Tolerance Towards Hydrogen Peroxide

The same setup as in example 4 was used. Turbidity is measured after 20 minutes, but here 15 ppm of hydrogen peroxide was added at constant level to different enzyme dosage levels of enzyme B); temperature 48° C.; pH=8.5 using 5 mM Hepes buffer. The results are shown in Table 9 below.

TABLE 9

| Dosage Enzyme B) (ppm) | Turbidity (NTU) with 15 ppm peroxide | Turbidity (NTU) without peroxide |
|---|---|---|
| 0 | 19 | 12 |
| 0.1 | 37 | 32 |
| 0.5 | 82 | 86 |
| 1 | 118 | 114 |
| 2.5 | 123 | 130 |

In another experiment a constant enzyme dosage level of 0.5 ppm of enzyme B) was combined with various levels of hydrogen peroxide (0-1000 ppm). The results are shown in Table 10 below.

TABLE 10

| Dosage of peroxide (ppm) | Turbidity (NTU) |
|---|---|
| 0 | 93 |
| 15 | 86 |
| 200 | 102 |
| 600 | 101 |
| 1000 | 92 |

Example 6

Tolerance Towards LAS

Linear Alkylbenzene Sulfonate

The same setup as in Example 4 was used. Buffer 5 mM Hepes pH=7; 45° C.; the turbidity was measured after 20 minutes. Two different levels of LAS were added to the assay: 50 and 200 ppm. The results are shown in Table 11 below.

TABLE 11

| | Turbidity (NTU) |
|---|---|
| Blank pH 7, 50 ppm LAS | 116 |
| Blank pH 7, 200 ppm LAS | 133 |
| 0.5 ppm Enzyme B; pH 7, 50 ppm LAS | 226 |
| 0.5 ppm Enzyme B; pH 7, 200 ppm LAS | 220 |

Example 7

Measurement of Degree of Hydrolysis of Vinyl Acetate Homopolymer

The degree of hydrolysis (deacetylation) of a polymer comprising vinyl acetate monomer can be measured by detection of acetate released into the solution. Acetate in small concentrations can be detected and quantified by Capillary Electrophoresis analysis.

40 ml of 5 mM Hepes buffer, pH=8 is heated to 50° C. in closed Erlenmeyer flasks on the heated water bath. The enzyme is dosed into the buffer in amounts according to the below table. Then 6% w/v PVAc in methanol (Mw≈12800) is injected into the buffer in amounts according to the table below. Samples are taken after 18 hours and filtered through the 0.22 micro-m filters. The amount of acetate in these samples is detected by Capillary electrophoresis, using Agilent buffer and Agilent capillar is used (see equipment list). Program: Temperature 30° C., Voltage −30 kV. Flush 4 min with buffer. Inject sample at 50 mbar, 6 sec., inject buffer at 50 mbar, 10 sec. Elution for 20 min. Detection signal: 350/20 nm. Reference signal: 275/10 nm.

An acetate standard curve 0-450 ppm acetate is run in parallel. The acetate peaks are integrated, and the amounts in the samples are determined relative to the standard curve. The degree of hydrolysis of the PVAc is determined by calculating the actual amount of vinyl acetate monomer in the flask from the beginning. Vinyl Acetate has Mw of 86 g/mol.

For Experiment no. 1-6 with injection of 1.5 ml PVAc solution, the calculations are as follows:

$$\frac{0.0015 \text{ liter} * 60 \text{ g VAc/liter}}{86 \text{ g/mol} * 0.0415 \text{ liter}} = 2.522 * 10^{-2} \text{ mol/liter}$$

The results are shown in table 12 below. A degree of hydrolysis of 1% will result in an acetate concentration of $2.522*10^{-4}$ mol/liter=15.1 mg/liter=15.1 ppm acetate. For Experiments 1-6, the degree of hydrolysis (%) is calculated relative to 1% hydrolysis corresponding to 15.1 ppm Acetate. For Experiments 7-12, the calculations give 1% hydrolysis corresponding to 29.2 ppm acetate.

TABLE 12

| Experiment No. | PVAc injected | Enzyme dosage | Degree of hydrolysis After 18 hours |
|---|---|---|---|
| 1 | 1.5 ml | 10 ppm enzyme B) | 1.9 |
| 2 | 1.5 ml | 10 ppm enzyme B) + 1 ppm enzyme J) | 1.4 |
| 3 | 1.5 ml | 10 ppm enzyme B) + 10 ppm enzyme J) | 1.6 |
| 4 | 1.5 ml | 1 ppm enzyme J) | 0 |
| 5 | 1.5 ml | 10 ppm enzyme J) | 0 |
| 6 | 1.5 ml | Blank | 0 |
| 7 | 3.0 ml | 10 ppm enzyme B) | 1.1 |
| 8 | 3.0 ml | 10 ppm enzyme B) + 1 ppm enzyme J) | 1.3 |
| 9 | 3.0 ml | 10 ppm enzyme B) + 10 ppm enzyme J) | 1.3 |
| 10 | 3.0 ml | 1 ppm enzyme J) | 0 |
| 11 | 3.0 ml | 10 ppm enzyme J) | 0 |
| 12 | 3.0 ml | Blank | 0 |

Example 8

Measurement of Degree of Hydrolysis of Vinyl Acetate Homopolymer at Different pH and Temperatures This example is run exactly as example 7, but with different conditions, viz. pH=6 using 5 mM MES buffer or pH=8 using 5 mM Hepes buffer at 35° C., 45° C. and 55° C. The results are shown in Table 13 below.

TABLE 13

| Experiment No. | PVAc injected | Temperature | pH | Enzyme dosage | Degree of hydrolysis After 18 hours |
|---|---|---|---|---|---|
| 1 | 1.5 ml | 35° C. | 8 | Blank | 0 |
| 2 | 1.5 ml | 35° C. | 8 | 10 ppm enzyme C) | 1.4 |
| 3 | 1.5 ml | 35° C. | 8 | 10 ppm enzyme B) | 2.0 |
| 4 | 1.5 ml | 35° C. | 6 | Blank | 0 |
| 5 | 1.5 ml | 35° C. | 6 | 10 ppm enzyme C) | 1.0 |
| 6 | 1.5 ml | 35° C. | 6 | 10 ppm enzyme B) | —* |
| 7 | 1.5 ml | 45° C. | 8 | Blank | 0 |
| 8 | 1.5 ml | 45° C. | 8 | 10 ppm enzyme C) | 1.4 |
| 9 | 1.5 ml | 45° C. | 8 | 10 ppm enzyme B) | 1.5 |
| 10 | 1.5 ml | 45° C. | 6 | Blank | 0 |
| 11 | 1.5 ml | 45° C. | 6 | 10 ppm enzyme C) | 1.1 |
| 12 | 1.5 ml | 45° C. | 6 | 10 ppm enzyme B) | 1.4 |
| 13 | 1.5 ml | 55° C. | 8 | Blank | 0 |
| 14 | 1.5 ml | 55° C. | 8 | 10 ppm enzyme C) | 2.2 |
| 15 | 1.5 ml | 55° C. | 8 | 10 ppm enzyme B) | 3.0 |
| 16 | 1.5 ml | 55° C. | 6 | Blank | 0 |
| 17 | 1.5 ml | 55° C. | 6 | 10 ppm enzyme C) | 1.3 |
| 18 | 1.5 ml | 55° C. | 6 | 10 ppm enzyme B) | 1.5 |

*experimental error, result discarded

Example 9

Prevention of Deposition of PVAc Agglomerates on Metal

PVAc agglomerates have a high tendency to precipitate and stick to different surfaces like metals and hydrophobic materials used for e.g. forming felts, pressing felts etc. The lipolytic enzymes described herein when added to the PVAc containing solution will prevent the formation of these stickies (the agglomerates do not stick to glass surfaces).

200 ml buffer 5 mM Hepes pH=8 is heated to 45° C. 10 ppm enzyme B) is added to one beaker. A beaker without enzyme addition is run in parallel as an enzyme blank. Agitation is carried out by glass coated magnets. A metal surface is dipped into the solutions. 4 ml 2% w/v PVAc (Mw≈113000) in methanol solution is injected into the solutions. The experiment is stopped after 10 minutes.

Figure 1:
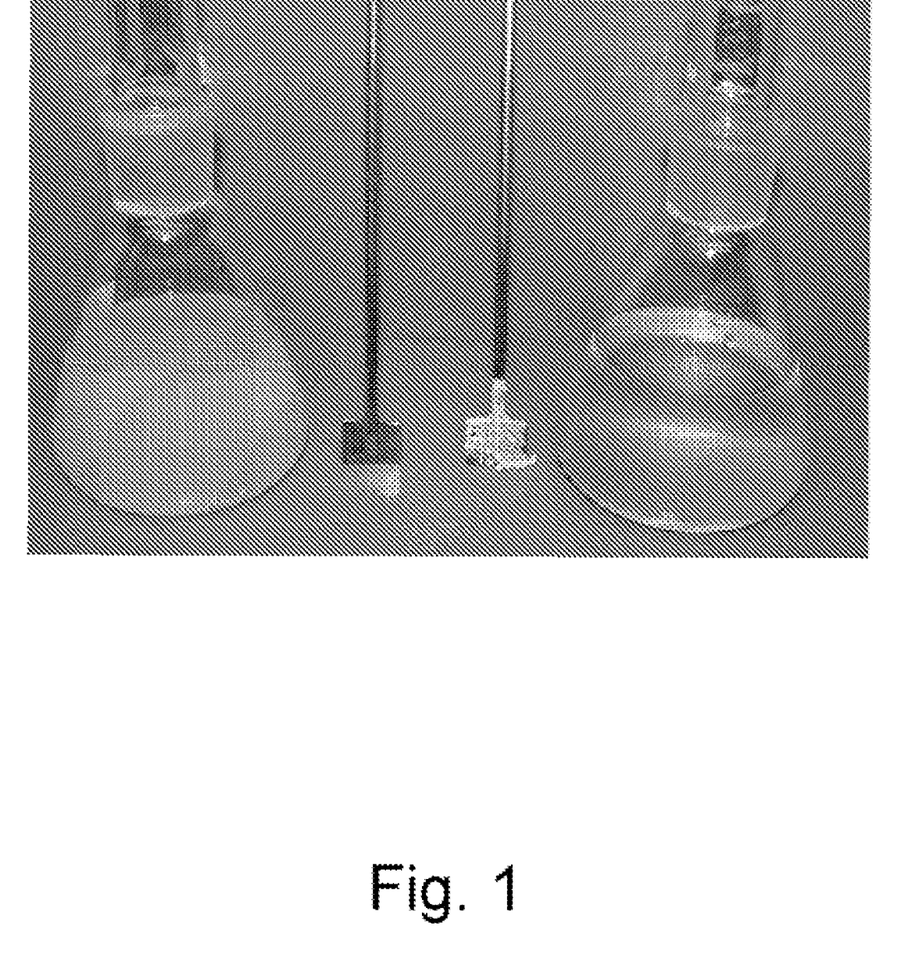
FIG. 1 is a photo of metal surface dipped in a PVAC solution with enzyme treatment according to the invention (left) and a metal surface dipped in a PVAc solution without enzyme treatment (right).

A photo of the metal surfaces is appended as FIG. 1. The rod to the left relates to the experiment with added enzyme B, and the rod to the right relates to the control experiment without added enzyme. The surface of the left rod appears clean, while the PVAC solution stays turbid. In contrast, the control experiment (rod to the right) shows PVAc agglomerates adhering to the metal surface, and the surrounding solution becomes clear.

Example 10

Prevention of PVAc Deposition on Metal Surface

The deposition of agglomerates on metal surfaces can be quantified as the mass uptake on a well defined surface. For this purpose a tensiometer equipped with a Wilhelmy plate can be applied. The tensiometer is operated to measure the weight increase of the Wilhelmy plate after slowly dipping the plate totally into a solution of PVAc every 2 minutes. The weight after 10 minutes is determined.

The Wilhelmy plate is cleaned by dipping in ethanol and glowing in a gas burner flame. The clean plate is placed on the tensiometer electronic balance. 100 ml buffer 5 mM Hepes pH=8 is heated to the desired temperature (35° C. or 45° C.) in the tensiometer beaker. Enzyme is added.

2 ml of 2% w/v PVAc (Mw≈113000) in methanol solution is injected. The up/down movement of the Wilhelmy plate is started. After 10 minutes the weight of the plate is determined. A low weight uptake indicates prevention of PVAc deposition. The results obtained at a temperature of 35 and 45° C., respectively, are shown in Tables 13 and 14, respectively.

TABLE 13

| Dosage Enzyme B) (ppm) | Dosage Enzyme C) (ppm) | Mass uptake (mg) t = 10 min |
|---|---|---|
| 0 | | 127 |
| 2 | | 114 |

TABLE 13-continued

| Dosage Enzyme B) (ppm) | Dosage Enzyme C) (ppm) | Mass uptake (mg) t = 10 min |
|---|---|---|
| 5 | | 67 |
| 6 | | 8 |
| 7.5 | | 8 |
| 10 | | 7 |
| | 0 | 127 |
| | 10 | 129 |
| | 50 | 66 |
| | 100 | 22 |

TABLE 14

| Dosage Enzyme B) (ppm) | Dosage Enzyme C) (ppm) | Mass uptake (mg) t = 10 min |
|---|---|---|
| 0 | | 32 |
| 0.5 | | 12 |
| 1 | | 4.3 |
| 2 | | 4.5 |
| 5 | | 5.4 |
| 10 | | 5.7 |
| | 0 | 32 |
| | 100 | 26 |

Example 11

Determination of Purity of Lipolytic Enzymes

The protein concentration of an enzyme sample is determined with a BCA protein assay kit from PIERCE (identical to PIERCE cat. No. 23225). The sodium salt of Bicinchoninic acid (BCA) is a stable, water-soluble compound capable of forming an intense purple complex with cuprous ions ($Cu^{1+}$) in an alkaline environment. The BCA reagent forms the basis of the BCA protein assay kit capable of monitoring cuprous ions produced in the reaction of protein with alkaline $Cu^{2+}$ (Biuret reaction). The colour produced from this reaction is stable and increases in a proportional fashion with increasing protein concentrations (Smith, P. K., et al. (1985), Analytical Biochemistry, vol. 150, 76-85). The BCA working solution is made by mixing 50 parts of re(Reagent agent A with 1 part reagent B (Reagent A is PIERCE cat. No. 23223, contains BCA and tartrate in an alkaline carbonate buffer; reagent B is PIERCE cat. No. 23224, contains 4% $CuSO_4*5H_2O$). 300 ml sample is mixed with 3.0 ml BCA working solution. After 30 minutes at 37° C., the sample is cooled to room temperature and $A_{490}$ is read as a measure of the protein concentration in the sample. Dilutions of Bovine serum albumin (PIERCE cat. No. 23209) are included in the assay as a standard.

If the lipolytic enzyme is on solid form, the product is first dissolved/suspended in 20 volumes of 100 mM $H_3BO_3$, 10 mM 3,3'-dimethylglutaric acid, 2 mM $CaCl_2$, pH 6 (Buffer A) for at least 15 minutes at 5° C., and if the enzyme at this stage is a suspension, the suspension is filtered through a 0.45 micro-m filter to give a clear solution. The solution is from this point treated as a liquid lipolytic enzyme.

If the lipolytic enzyme is a liquid, the product is first dialysed in a 6-8000 Da cut-off SpectraPor dialysis tube (cat no. 132 670 from Spectrum Medical Industries) against 100 volumes of Buffer A+150 mM NaCl (Buffer B) for at least 5 hours at 5° C., to remove formulation chemicals that could give rise to a high viscosity, which is detrimental to the size-exclusion chromatography.

The dialysed lipolytic enzyme is filtered through a 0.45 micro-m filter if a precipitate was formed during the dialysis. The protein concentration in the dialysed enzyme product is determined with the above described protein concentration assay and the enzyme product is diluted with Buffer B, to give a sample ready for size-exclusion chromatography with a protein concentration of 5 mg/ml. If the enzyme product has a lower than 5 mg/ml protein concentration after dialysis, it is used as is.

A 300 ml HiLoad26/60 Superdex75 pg column (Amersham Pharmacia Biotech) is equilibrated in Buffer B (Flow: 1 ml/min). 1.0 ml of the enzyme sample is applied to the column and the column is eluted with Buffer B (Flow: 1 ml/min). 2.0 ml fractions are collected from the outlet of the column, until the sample has eluted from the column. The collected fractions are analysed for lipolytic activity. A protein peak with activity in one or more of the assays described herein is defined as a lipolytic enzyme peak. The purity of a lipolytic enzyme peak is calculated as the protein amount in the peak divided with the total protein amount in all identified peaks. In a particular embodiment the purity refers to protein amount in the peak divided with the total protein amount in all identified lipolytic peaks.

The invention claimed is:

1. A method for making paper comprising:
   a) preparing a pulp from a material comprising recycled paper;
   b) treating the pulp with a lipolytic enzyme, which is able to hydrolyze a polymer comprising vinyl acetate monomer; and
   c) making paper from the treated pulp; wherein the enzyme has
      a) a degree of hydrolysis by Capillary Electrophoresis of at least 0.1 after 18 hours at 45° C. on a dispersed PVAc substrate, wherein the dispersed PVAc substrate is prepared by injecting 1.5 ml of 6% PVAc in methanol into 40 ml buffer pH 6 or 8, and wherein the molecular weight of the PVAc is about 12800; and/or
   b) a hydrolytic activity at 35° C. for 4 min with a 5% (w/v) polymer preparation comprising vinyl acetate as substrate in an emulsion consisting of 50 mM NaCl, 0.5 mM $KH_2PO_4$, 9% (v/v) Glycerol and 0.1% (w/v) Gum Arabicum, wherein the polymer is:
      (i) a PVAc homopolymer preparation and the reaction pH is 8;
      (ii) a vinyl acetate ethylene copolymer preparation, and the reaction pH is 7; and/or
      (iii) a vinyl acetate tert-decanoic acid, ethenyl ester copolymer preparation, and the reaction pH is 7.

2. The method of claim 1, wherein the hydrolytic activity under the conditions of (i) is higher than 0.2 units.

3. The method of claim 1, wherein the enzyme has a PVAc hydrolytic activity of at least 0.7 units/ml.

4. The method of claim 1, wherein the hydrolytic activity under the conditions of (ii) is at least 0.2 units/ml.

5. The method of claim 1, wherein the hydrolytic activity under the conditions of (iii) is at least 0.2 units/ml.

6. The method of claim 1, wherein for the determination of degree of hydrolysis according to a), and for the determination of hydrolytic activity according to any one of steps (i)-(iii), the enzyme is purified.

7. The method of claim 1, wherein for the determination of degree of hydrolysis according to a), and for the determination of hydrolytic activity according to any one of steps (i)-(iii), the enzyme is desalted.

8. The method of claim 1, wherein for the determination of hydrolytic activity according to any one of steps (i)-(iii), 200 micro-liter of an enzyme solution of an $A_{280}$=0.15, or 50 micro-gram enzyme protein, is added to 15 ml of substrate emulsion.

9. The method of claim 1, wherein the lipolytic enzyme is added in an amount effective to reduce the amount of stickies.

10. The method of claim 1, wherein the enzyme dosage for paper manufacturing is from 0.1 to 5000 units of PVAc hydrolytic activity per gram of polymer comprising vinyl acetate monomer.

11. The method of claim 1, wherein the enzyme dosage per ton of paper pulp is:
  (i) from about 100 to about 100.000 units according to (i) of claim 1; or
  (ii) from about 0.1 to about 100.000 mg enzyme protein.

12. The method of claim 1, wherein the enzyme is active and stable in the presence of LAS and/or hydrogen peroxide.

13. The method of claim 1, further comprising the use of at least one additional enzyme selected from the following group consisting of proteases, amylases, pullulanases, lipases, hemicellulases, endoglucanases, pectinases, and cutinases.

14. The method of claim 1, further comprising the use of at least one anionic, non-ionic, cationic and/or zwitterionic surfactant and/or dispersant.

15. The method of claim 1, wherein the paper material contains ink and the lipolytic enzyme is added in an amount effective to de-ink the paper material.

* * * * *

SEQUENCE LISTING

```
<160> NUMBER OF SEQ ID NOS: 3

<210> SEQ ID NO 1
<211> LENGTH: 194
<212> TYPE: PRT
<213> ORGANISM: Humicola insolens

<400> SEQUENCE: 1

Gln Leu Gly Ala Ile Glu Asn Gly Leu Glu Ser Gly Ser Ala Asn Ala
1               5                   10                  15

Cys Pro Asp Ala Ile Leu Ile Phe Ala Arg Gly Ser Thr Glu Pro Gly
            20                  25                  30

Asn Met Gly Ile Thr Val Gly Pro Ala Leu Ala Asn Gly Leu Glu Ser
        35                  40                  45

His Ile Arg Asn Ile Trp Ile Gln Gly Val Gly Gly Pro Tyr Asp Ala
    50                  55                  60
```

```
Ala Leu Ala Thr Asn Phe Leu Pro Arg Gly Thr Ser Gln Ala Asn Ile
 65                  70                  75                  80

Asp Glu Gly Lys Arg Leu Phe Ala Leu Ala Asn Gln Lys Cys Pro Asn
                 85                  90                  95

Thr Pro Val Val Ala Gly Gly Tyr Ser Gln Gly Ala Ala Leu Ile Ala
            100                 105                 110

Ala Ala Val Ser Glu Leu Ser Gly Ala Val Lys Glu Gln Val Lys Gly
                115                 120                 125

Val Ala Leu Phe Gly Tyr Thr Gln Asn Leu Gln Asn Arg Gly Gly Ile
            130                 135                 140

Pro Asn Tyr Pro Arg Glu Arg Thr Lys Val Phe Cys Asn Val Gly Asp
145                 150                 155                 160

Ala Val Cys Thr Gly Thr Leu Ile Ile Thr Pro Ala His Leu Ser Tyr
                165                 170                 175

Thr Ile Glu Ala Arg Gly Glu Ala Ala Arg Phe Leu Arg Asp Arg Ile
            180                 185                 190

Arg Ala

<210> SEQ ID NO 2
<211> LENGTH: 199
<212> TYPE: PRT
<213> ORGANISM: Fusarium solani pisi

<400> SEQUENCE: 2

Gly Arg Thr Thr Arg Asp Asp Leu Ile Asn Gly Asn Ser Ala Ser Cys
 1               5                  10                  15

Ala Asp Val Ile Phe Ile Tyr Ala Arg Gly Ser Thr Glu Thr Gly Asn
                20                  25                  30

Leu Gly Thr Leu Gly Pro Ser Ile Ala Ser Asn Leu Glu Ser Ala Phe
             35                  40                  45

Gly Lys Asp Gly Val Trp Ile Gln Gly Val Gly Gly Ala Tyr Arg Ala
         50                  55                  60

Thr Leu Gly Asp Asn Ala Leu Pro Arg Gly Thr Ser Ser Ala Ala Ile
 65                  70                  75                  80

Arg Glu Met Leu Gly Leu Phe Gln Gln Ala Asn Thr Lys Cys Pro Asp
                 85                  90                  95

Ala Thr Leu Ile Ala Gly Gly Tyr Ser Gln Gly Ala Ala Leu Ala Ala
            100                 105                 110

Ala Ser Ile Glu Asp Leu Asp Ser Ala Ile Arg Asp Lys Ile Ala Gly
                115                 120                 125

Thr Val Leu Phe Gly Tyr Thr Lys Asn Leu Gln Asn Arg Gly Arg Ile
            130                 135                 140

Pro Asn Tyr Pro Ala Asp Arg Thr Lys Val Phe Cys Asn Thr Gly Asp
145                 150                 155                 160

Leu Val Cys Thr Gly Ser Leu Ile Val Ala Ala Pro His Leu Ala Tyr
                165                 170                 175

Gly Pro Asp Ala Arg Gly Pro Ala Pro Glu Phe Leu Ile Glu Lys Val
            180                 185                 190

Arg Ala Val Arg Gly Ser Ala
            195

<210> SEQ ID NO 3
<211> LENGTH: 317
<212> TYPE: PRT
<213> ORGANISM: Candida antarctica
```

-continued

```
<400> SEQUENCE: 3

Leu Pro Ser Gly Ser Asp Pro Ala Phe Ser Gln Pro Lys Ser Val Leu
1               5                   10                  15

Asp Ala Gly Leu Thr Cys Gln Gly Ala Ser Pro Ser Ser Val Ser Lys
            20                  25                  30

Pro Ile Leu Leu Val Pro Gly Thr Gly Thr Thr Gly Pro Gln Ser Phe
            35                  40                  45

Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65                  70                  75                  80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
130                 135                 140

Asp Ala Leu Ala Val Ser Ala Pro Ser Val Trp Gln Gln Thr Thr Gly
145                 150                 155                 160

Ser Ala Leu Thr Thr Ala Leu Arg Asn Ala Gly Gly Leu Thr Gln Ile
                165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
            195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
225                 230                 235                 240

Leu Arg Ser Thr Thr Gly Gln Ala Arg Ser Ala Asp Tyr Gly Ile Thr
                245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
            275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305                 310                 315
```